(12) United States Patent
Oslund et al.

(10) Patent No.: US 12,396,732 B2
(45) Date of Patent: Aug. 26, 2025

(54) EXPANDING MEDICAL DEVICE WITH SUPPORT

(71) Applicant: KA Medical, LLC, Roseville, MN (US)

(72) Inventors: John Oslund, Blaine, MN (US); Pat Russo, Vadnais Heights, UT (US); Kevin Dunne, Saint Paul, MN (US)

(73) Assignee: KA Medical, LLC, Roseville, MN (US)

( * ) Notice: Subject to any disclaimer, the term of this patent is extended or adjusted under 35 U.S.C. 154(b) by 70 days.

(21) Appl. No.: 17/203,439

(22) Filed: Mar. 16, 2021

(65) Prior Publication Data
US 2021/0290248 A1  Sep. 23, 2021

Related U.S. Application Data

(60) Provisional application No. 62/990,858, filed on Mar. 17, 2020.

(51) Int. Cl.
*A61B 17/12* (2006.01)
*A61B 17/00* (2006.01)

(52) U.S. Cl.
CPC .. *A61B 17/12145* (2013.01); *A61B 17/12109* (2013.01); *A61B 2017/00867* (2013.01); *A61B 2017/00871* (2013.01)

(58) Field of Classification Search
CPC ........ A61B 17/12145; A61B 17/12109; A61B 2017/00867; A61B 2017/00871; A61B 17/12172
See application file for complete search history.

(56) References Cited

U.S. PATENT DOCUMENTS

| | | | |
|---|---|---|---|
| 2006/0129166 A1* | 6/2006 | Lavelle | A61B 17/221 606/113 |
| 2006/0235463 A1 | 10/2006 | Freudenthal et al. | |
| 2013/0041454 A1 | 2/2013 | Dobson et al. | |
| 2014/0330299 A1* | 11/2014 | Rosenbluth | A61B 17/12154 606/191 |
| 2016/0317158 A1* | 11/2016 | Lorenzo | A61B 17/12172 |
| 2017/0354421 A1* | 12/2017 | Maguire | A61B 17/12159 |
| 2018/0055515 A1* | 3/2018 | Greene, Jr. | A61B 17/12168 |

(Continued)

OTHER PUBLICATIONS

International Search Report and Written Opinion dated Jul. 2, 2021 for PCT/US2021/022598.

*Primary Examiner* — Melanie R Tyson
*Assistant Examiner* — Mikail A Mannan
(74) *Attorney, Agent, or Firm* — Dorsey & Whitney LLP

(57) ABSTRACT

This application describes various embodiments of an expandable device that includes at least one support member. The support member (or members) is integrated into the structure of the expandable device and increases its column strength, which thus augments pushability of the expanding device through a delivery catheter. The support member allows force applied while pushing from the proximal end of the expandable device to be translated to the distal end of the device and therefore avoid bunching or deformation without increasing the profile of the device to a degree that would prohibit passage through a lumen of a specific required size. Thus, the expandable devices described herein address at least some of the shortcomings discussed above.

12 Claims, 3 Drawing Sheets

(56) References Cited

U.S. PATENT DOCUMENTS

2019/0142435 A1 5/2019 Demeritt
2020/0038031 A1 2/2020 Gorochow
2020/0038209 A1 2/2020 Slazas et al.

* cited by examiner

EXPANDING MEDICAL DEVICE WITH SUPPORT

RELATED APPLICATIONS

The present application claims priority to U.S. Provisional Application No. 62/990,858, filed on Mar. 17, 2020 and titled, "Expanding Medical Device With Support," which is hereby incorporated by reference in its entirety.

TECHNICAL FIELD

The present application is related to medical devices and methods. More specifically, the application is related to expandable medical devices with a support.

DETAILED DESCRIPTION

Figure 1:
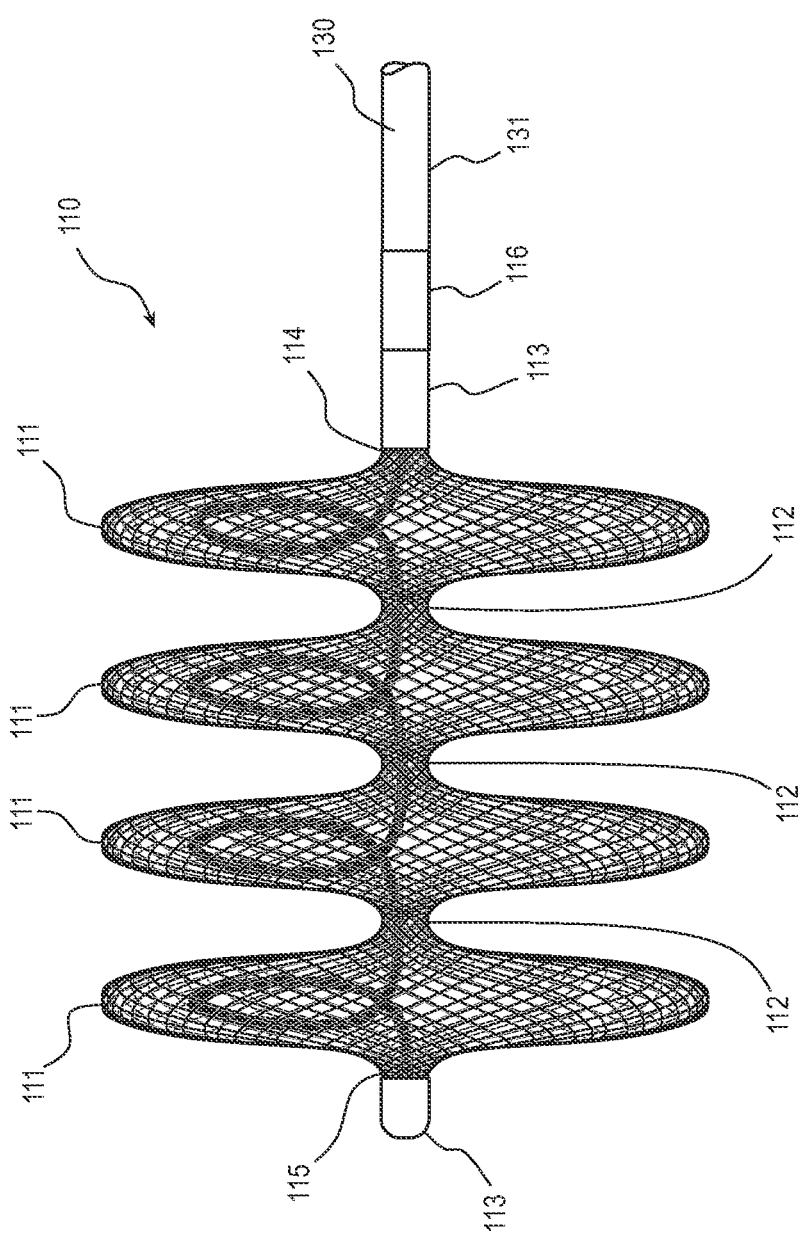
FIG. 1 is a side view of an embodiment of an embolization device in an expanded state with a support member.

Some medical devices are expandable within the body. In some instances, these devices expand and are left in the body as implants, and in other instances such devices are expanded during use for a medical or surgical procedure and then are removed. Expanding medical devices can be introduced into the body in a constrained, "low profile" configuration (e.g., with a smaller diameter) inside a delivery device, such as a delivery catheter. When the expanding device is released from constraint, such as by advancing it out of the distal end of the delivery catheter, the device either self-expands or, in some embodiments, may be expanded by a balloon or other expanding device to assume a larger diameter, deployed configuration. Examples of such expanding devices include stents for propping open coronary arteries, artificial valves for implantation in the heart, stent grafts used to treat abdominal aortic aneurysms and other arterial conditions, vascular and cardiac occluders, vascular filters, and embolic protection devices. Other examples of expanding devices exist for other lumens in the body.

In certain instances, a force required to deliver the expandable device through the lumen of the delivery catheter might be too high and/or the expandable device may have insufficient column strength to be readily "pushable" through the delivery device. Either or both of these issues may result in the expanding device not being deliverable and/or the lumen of the delivery catheter being damaged by a forceful advancement of the expanding device.

Certain embodiments of expanding devices disclosed within the scope of this application include a support member. The support member is configured to increase pushability of the expanding device, such as to facilitate its delivery through a delivery catheter or other delivery device, without interfering with the function of the expanding device once delivered. Although the expanding devices described herein may be used for vascular applications, the support members described in this application may be applied to any other type of expandable medical device.

In some embodiments within the scope of this disclosure, the expanding device includes a braided wire structure comprising a plurality of lobes, enclosures, or baskets. Enclosures or lobes within the scope of this disclosure include baskets of a braided lattice or matrix, including embodiments formed of nitinol wires. The plurality of lobes may be coupled together and releasably coupled to a placement wire. The lobes can be crimped or constrained to a small diameter and disposed within a delivery catheter for deployment into a blood vessel. In some embodiments, in a fully expanded configuration, the lobes have a disc shape. In a partially expanded state, the lobes may be elongate, spherical, ovoid, cylindrical, or other shapes. The lobes may be configured to restrict blood flow through the blood vessel when deployed within the blood vessel. When deployed, the lobes may be fully or partially expanded, including instances where the degree of expansion is controlled by interaction between the vessel wall and the lobes.

In certain embodiments within the scope of this disclosure, a support member may be disposed through the braided wire structure from a proximal end to a distal end. When deploying the expanding device through a delivery device (e.g., delivery catheter), the support member is configured to transfer a distally directed force from the proximal end to the distal end of the braided wire structure. The transfer of the distally directed force to the distal end increases the column strength and pushability of the expanding device and allows the expanding device to be pushed through the delivery device while minimizing damage to the expanding device and/or the delivery device. Upon deployment from the delivery device, the lobes radially expand to contact a wall of a blood vessel resulting in shortening of the expanding device and coiling of the support member within the lobes.

Expanding devices within the scope of this disclosure can be manufactured by braiding filaments to create a lattice or basket defining the lobe or enclosure. Filaments within the scope of this disclosure include metals and polymers, including superelastic or shape memory materials. For example, nitinol wires may be used to form the lobes of the braided wire structure. In some embodiments, a continuous braid of filaments may be used to form a plurality of lobes with reduced diameter middle portions disposed between the lobes. During manufacturing, the support member can be disposed through the lobes and the reduced diameter middle portions. The braided wire structure, with the support member, may be crimped to a small diameter to fit within the delivery device.

An expanding device within the scope of this disclosure may be used in procedures to occlude vascular structures such as blood vessels. The expanding device can be deployed into a blood vessel by positioning a support catheter at a desired deployment location for the expanding device, inserting the loaded delivery catheter into the support catheter, deploying the expanding device with the support member through the delivery device, transferring a distally directed force applied to the proximal end of the expanding device by a placement wire through the support wire to the distal end of the expanding device, deploying the expanding device into the blood vessel, and releasing the expanding device from the placement wire. Once deployed, the expanding device can self-expand until it contacts the vessel wall. When expanded, the expanding device may shorten in length and the support member may coil within the expanded lobes. Additionally, when expanded, the braided lattice of the expanded device and the support member may restrict blood flow through the blood vessel. In certain instances, the restricted blood flow through the blood vessel results in formation of a thrombus or clot to occlude the blood vessel.

Embodiments may be understood by reference to the drawings. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings or figures, these are not necessarily drawn to scale unless specifically indicated.

In the following disclosure, various features are sometimes grouped together in a single embodiment, figure, or description thereof for the purpose of streamlining the disclosure. Many of these features may be used alone and/or in combination with one another.

Figure 2:
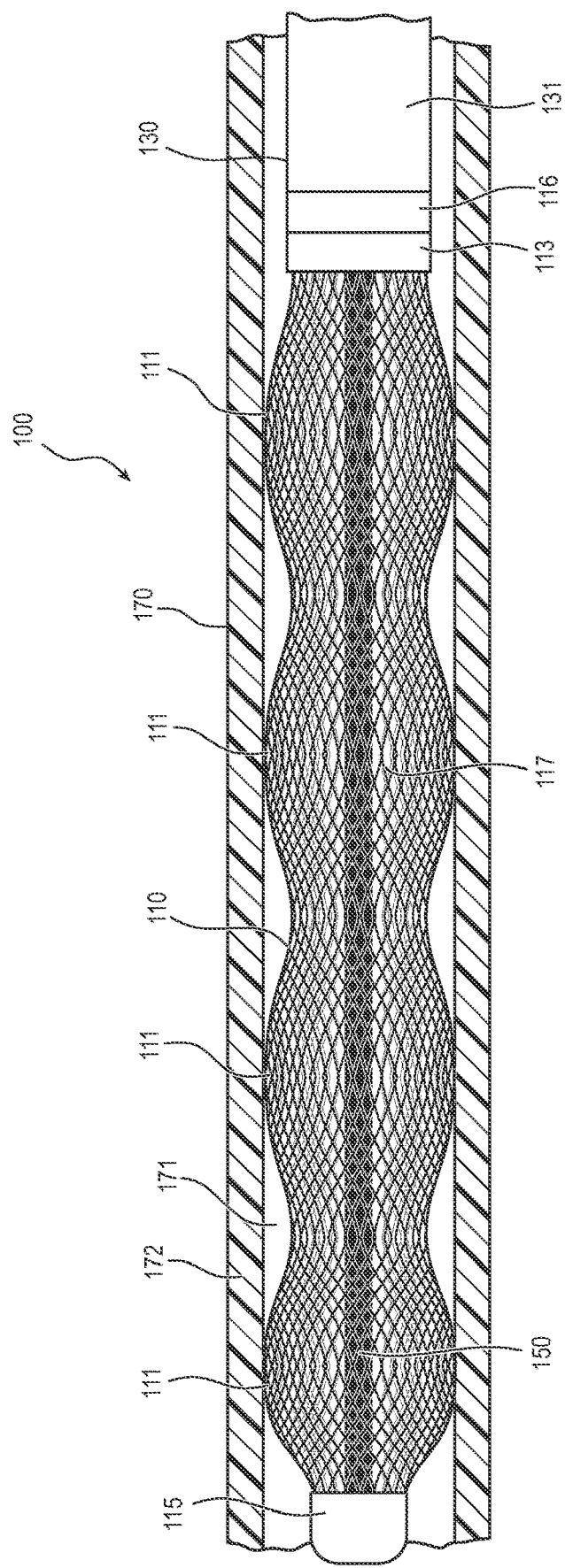
FIG. 2 is a side view of the embolization device of FIG. 1 in a constrained state within a delivery device.
Figure 3:
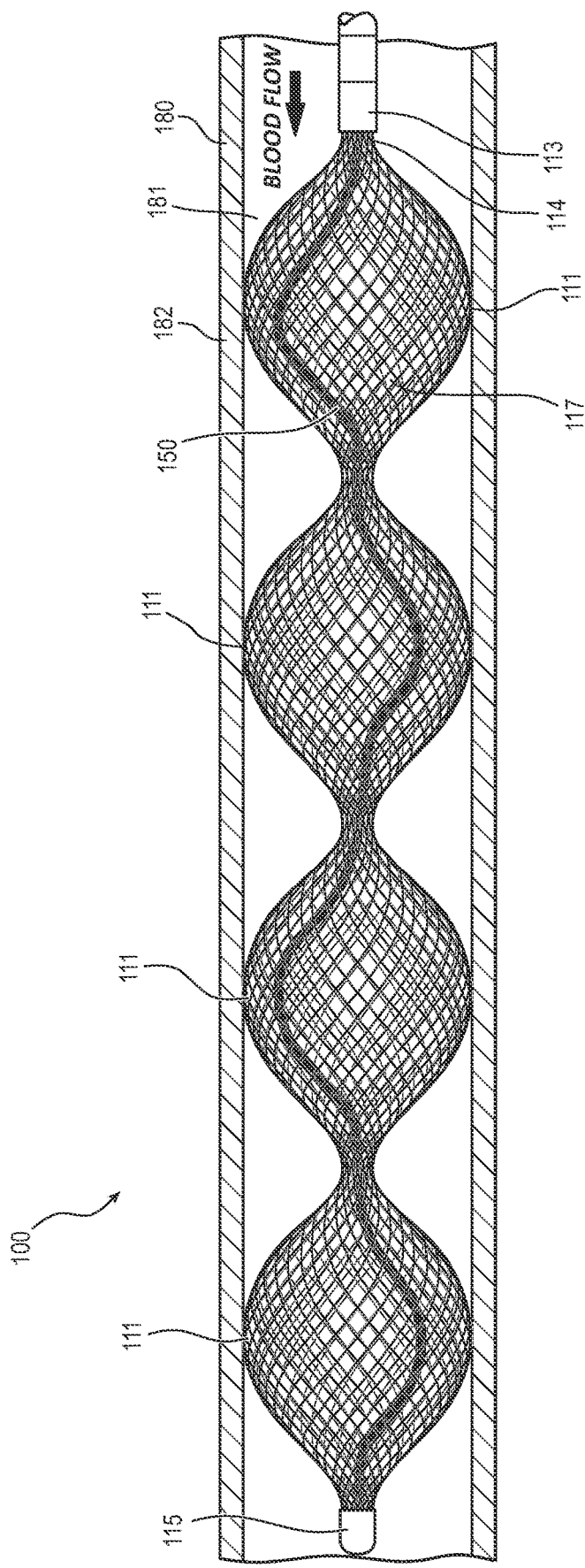
FIG. 3 is a side view of the embolization device of FIG. 1 in a partially expanded state within a blood vessel lumen.

FIGS. 1-3 illustrate different views of an embodiment of an expanding device and related components. FIG. 1 illustrates the expanding device in an expanded state with a support member disposed through the expanding device. FIG. 2 illustrates the expanding device in a constricted state within a delivery device with the support member extending through the expanding device. FIG. 3 illustrates the expanding device in a partially expanded state within a blood vessel with the support member extending through the expanding device. In certain views, each device may be coupled to, or shown with, additional components not included in every view. Further, in some views, only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 depicts an embodiment of an expanding device 100 in an expanded state. As illustrated in FIG. 1, the expanding device 100 includes a braided wire structure 110 and a support member 150 disposed through the braided wire structure 110. The support member 150 may be free floating within the braided wire structure 110, allowing the braided wire structure 110 to lengthen when the braided wire structure 110 is radially compressed.

As illustrated, the braided wire structure 110 is an embolic structure. In other embodiments, the braided wire structure 110 may be any suitable structure configured for deployment within a vessel of a patient, such as stents, stent-grafts, filters, and so forth. As illustrated in FIG. 1, the braided wire structure 110 is composed of four lobes or segments 111 with reduced diameter portions 112 disposed between the lobes 111. In another embodiment, the braided wire structure 110 may include a single lobe 111. In yet another embodiment, the braided wire structure 110 may include two lobes 111 with a reduced diameter portion 112 disposed between the two lobes 111. In yet another embodiment, the braided wire structure 110 may include three lobes 111 with reduced diameter portions 112 disposed between the lobes 111. Embodiments with more than four lobes 111, including embodiments with five, six, seven, or more lobes 111, are likewise within the scope of this disclosure. In the illustrated embodiment, in the expanded state, the lobes 111 have a disc shape. Embodiments where the expanded shape is spherical, ovoid, cylindrical, or any other shape are likewise within the scope of this disclosure.

In the illustrated embodiment, the braided wire structure 110 includes a braided lattice or matrix of wires made from any suitable material and may be self-expanding. For example, the material may be nitinol or any other suitable shape memory metal or polymer. In other embodiments, the braided lattice may be balloon-expandable and may be made from any suitable material, such as stainless steel, titanium, etc. The ends of the wires can be restrained by clamps 113 disposed at the proximal end 114 and the distal end 115 to prevent fraying of the braided lattice. The braided wire structure 110 can be releasably coupled to a placement wire 130 for deployment. For example, in the illustrated embodiment the braided wire structure 110 includes a threaded coupling 116 disposed at the proximal end 114 that can be threadingly coupled to a threaded end 131 of the placement wire 130. When deployed, the braided wire structure 110 can be rotationally held in place relative to the placement wire 130 when the braided wire structure 110 engages with the vessel wall and the placement wire 130 can be rotated to release the placement wire 130 from the braided wire structure 110. Other mechanisms for release and deployment are also within the scope of this disclosure including hooks, collets, loops, snares, and so forth.

As illustrated, the support member 150 is disposed through the braided wire structure 110 and fixedly coupled to the proximal end 114 and the distal end 115. As depicted, the support member 150 is centrally disposed through the braided wire structure 110. In some embodiments, the support member 150 may be radially offset from a central longitudinal axis of the braided wire structure 110. The support member 150 is disposed within the lobes 111 and passes through the reduced diameter portions 112. The support member 150 may have a spiral, coiled or curved shape, when the braided wire structure 110 is in the expanded state or partially expanded state. In other embodiments, the expanding device 100 may include more than one support member 150. For example, the expanding device 100 may include two, three, four, or more support members 150 disposed within the braided wire structure 110.

In some embodiments, the support member 150 can be a metal wire, having an equivalent or larger diameter and/or a greater stiffness than the wires used to make the braided wire structure 110. For example, the diameter of the support member 150 can be 2 times to 15 times larger than the diameter of wires of the braided wire structure 110. In other embodiments, the support member 150 can be a metal wire, having a smaller diameter and/or a greater stiffness than the wires used to make the braided wire structure 110. The support member 150 may be made of any suitable material. For example, the support member 150 may be made of nickel-titanium alloy, spring stainless steel, shape memory metals, and shape memory polymers. Other materials are contemplated. In some embodiments the support member 150 can include nitinol. In other embodiments, the support member 150 may be made of a bioabsorbable polymer, wherein after the expanding device 100 is implanted, the support member 150 gradually resorbs into the body. In some embodiments, the support member 150 may be made of a radiopaque material, to improve radiographic visibility of the expanding device 100 after implantation with various imaging technologies. In certain embodiments, the support member 150 may be drug coated and/or filled, to supplement a therapeutic value of the expanding device 100. For example, the support member 150 may be coated with a thrombogenic material to promote thrombus formation within the expanding device 100 resulting in restriction of blood flow of the blood vessel.

In other embodiments, the support member 150 can play an active function after delivery of the expanding device 100. For example, the support member 150 may be self-expanding and configured to extend to a perimeter of the lobes 111 to add radial force to the lobes 111. This could be advantageous in vascular applications where device migration is a concern, such as vessel occlusion.

FIG. 2 illustrates the expanding device 100 in a radially collapsed or constrained or low-profile state. As illustrated, the expanding device 100 is disposed within a lumen 171 of a delivery device 170 (e.g., delivery catheter). The braided wire structure 110 is radially compressed by a wall 172 of the delivery device 170 wherein the lobes 111 are in contact with the wall 172 resulting in frictional resistance as the braided wire structure 110 is pushed through the delivery device 170. In the constrained state, the braided wire structure 110 is axially lengthened relative to the length of the braided wire structure 110 in the expanded state. When the braided wire structure 110 is axially lengthened, the support member 150 is uncoiled and becomes substantially straight and rigid. When straight and rigid, the support member 150 is configured to transfer a distally directed force from the placement wire 130 to the distal end 115 of the braided wire structure 110 to increase the column strength and pushability of the braided wire structure 110 through the lumen 171 of the delivery device 170. The increased column strength and pushability permits the expanding device 100 to be pushed through the delivery device 170 without longitudinal compression of the braided wire structure 110 and damage to the braided wire structure 110 and/or delivery device 170.

FIG. 3 illustrates the expanding device 100 in a partially expanded state. As illustrated, the expanding device 100 is disposed within a lumen 181 of a blood vessel 180. The braided wire structure 110 is partially radially compressed by a wall 182 of the blood vessel 180 wherein the lobes 111 are in contact with the wall 182 resulting in frictional resistance to displacement or migration of the braided wire structure 110. In the partially expanded state, the braided wire structure 110 is axially shortened relative to the length of the braided wire structure 110 in the constrained state. When the braided wire structure 110 is shortened, the support member 150 transitions from the straight and stiff configuration to a non-straight and flexible configuration. The support member 150 may have a spiral, coiled or curved shape, when the braided wire structure 110 is in the partially expanded state. In some embodiments the support member 150 may coil up to help draw the proximal end 114 and the distal end 115 toward each other to shorten the length of the braided wire structure 110. Shortening of the expanding device 100 may be beneficial when only a limited landing zone length within the blood vessel is available for the expanding device 100. The coiling up feature may also help prevent the support member 150 from contacting an inner wall of the blood vessel. In some embodiments, the support member 150 may be "free floating" within the braided wire structure 110, wherein when the expanding device 100 is implanted, the support member 150 does not contact the inner wall of the blood vessel or in some embodiments, an inner surface of the braided wire structure 110.

An expanding device within the scope of this disclosure can be deployed within a blood vessel by advancing a delivery device containing a braided wire structure and a support member to a treatment location in the body and deploying the embolic structure and the braided wire member. In some embodiments, the deployment may include connecting the braided wire structure to a placement wire and loading the braided wire structure and the support member into the delivery device by radially compressing the braided wire structure to a constrained or low-profile state and straightening the support member to facilitate loading the delivery device. As the braided wire structure is loaded into the delivery device, the placement wire can apply a distally directed force against a proximal end of the braided wire structure and the straightened support member can transfer that force to a distal end of the braided wire structure to increase the column strength and pushability of the braided wire structure to prevent damage to the expanding device and the delivery device.

The delivery device containing the constrained braided wire structure and the straightened support member is loaded into a support catheter and advanced beyond a distal end of the support catheter. The delivery device may be displaced proximally relative to the braided wire structure and the support member such that the braided wire structure and the support member are disposed within the blood vessel. The braided wire structure may be configured to self-expand as it is deployed within the blood vessel.

When deployed within the blood vessel, the braided wire structure and the support member can transition from the constrained state to the partially expanded state. In some embodiments, the lobes may self-expand when disposed outside the delivery device until the lobes contact a vessel wall. The support wire may become non-straight and have a spiral, coiled, or curved shape. In some embodiments, when the support wire becomes non-straight, the support wire draws the distal end and the proximal end of the braided wire structure together. The placement wire may be decoupled from the braided wire structure, for example, by rotating the placement wire relative to the braided wire structure to release the placement wire from the braided wire structure.

When deployed, the braided wire structure and the support member can form a physical blood flow restrictor within the blood vessel. A density of filaments in the braided wire structure, degree of expansion of the braided wire structure and support member, and other parameters may affect the degree to which flow across the expanding device is restricted. Embodiments wherein blood flow is reduced from about 10% to about 50% or more are within the scope of this disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of restricting blood flow within a blood vessel may include one or more of the following steps: positioning an embolization device into the blood vessel adjacent to a treatment site, deploying the embolization device from a delivery catheter into the blood vessel at the treatment site; self-expanding a lobe of an embolic structure of the embolization device within the blood vessel wherein the lobe contacts a wall of the blood vessel; expanding an embolic member coupled to the embolic structure; and restricting blood flow through the embolic member.

References to approximations are made throughout this specification, such as by use of the term "about." For each such reference, it is to be understood that, in some embodiments, the value, feature, or characteristic may be specified without approximation. For example, where a qualifier such as "about" is used, this term includes within its scope the qualified words in the absence of its qualifiers. For example, where the term "about" is recited with respect to a feature, it is understood that in further embodiments, the feature can have a precise configuration.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use.

The terms "a" and "an" can be described as one, but not limited to one. For example, although the disclosure may recite a structure having "a lobe," the disclosure also contemplates that the structure can have two or more lobes.

Unless otherwise stated, all ranges include both endpoints and all numbers between the endpoints.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

We claim:

1. An expanding medical device, comprising:
a braided wire structure configured to self-expand from a constrained state to an expanded state comprising a first end and a second end, wherein the braided wire structure comprises a lobe; and
a support member extending from the first end to the second end, wherein the support member provides longitudinal stiffness to the braided structure when the braided wire structure is in the constrained state,
wherein the support member has a curved shape that forms a single loop within the lobe, wherein the loop is radially offset from a longitudinal axis of the braided wire structure when the braided wire structure is in the expanded state,
wherein the support member in the expanded state is free floating and does not bear on an inner surface of the braided wire structure, and
wherein the support member is uncoiled and substantially straight when the braided wire structure is in the constrained state.

2. The expanding medical device of claim 1, wherein the support member is configured to transfer a distally directed force applied to the first end to the second end when the braided wire structure is in the constrained state.

3. The expanding medical device of claim 1, wherein the braided wire structure comprises a shape memory material selected from the group consisting of nickel-titanium alloy, spring stainless steel, shape memory metals, and shape memory polymers.

4. The expanding medical device of claim 1, wherein the braided wire structure comprises nitinol.

5. The expanding medical device of claim 1, wherein a diameter of the support member is the same or larger as a diameter of a wire of the braided wire structure.

6. The expanding medical device of claim 1, wherein the support member comprises a shape memory material selected from the group consisting of nickel titanium alloy, spring stainless steel, shape memory metals, and shape memory polymers.

7. The expanding medical device of claim 6, wherein the support member comprises nitinol.

8. The expanding medical device of claim 1, wherein the braided wire structure comprises a second lobe and a reduced diameter portion disposed between the first lobe and the second lobe, and wherein in the expanded configuration, the support member forms a single loop within the second lobe.

9. The expanding medical device of claim 8, wherein the expanding medical device is configured to occlude a blood vessel.

10. The expanding medical device of claim 1, wherein the braided wire structure comprises a lumen extending between the first end and the second end, and
wherein the support member is disposed within the lumen.

11. The expanding medical device of claim 1, wherein the support member is configured to draw the first end axially closer to the second end when the braided wire structure is in the expanded state.

12. The expanding medical device of claim 1, wherein the support member in the expanded state does not contact an inner surface of the braided wire structure.

* * * * *